(12) United States Patent
Haimerl et al.

(10) Patent No.: US 10,064,687 B2
(45) Date of Patent: Sep. 4, 2018

(54) ESTIMATION AND COMPENSATION OF TRACKING INACCURACIES

(71) Applicant: Brainlab AG, Munich (DE)

(72) Inventors: Martin Haimerl, Gilching (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 45 days.

(21) Appl. No.: 15/032,158

(22) PCT Filed: Jan. 13, 2014

(86) PCT No.: PCT/EP2014/050462
§ 371 (c)(1),
(2) Date: Apr. 26, 2016

(87) PCT Pub. No.: WO2015/104062
PCT Pub. Date: Jul. 16, 2015

(65) Prior Publication Data
US 2016/0256223 A1 Sep. 8, 2016

(51) Int. Cl.
*G01C 21/00* (2006.01)
*A61B 34/20* (2016.01)
(Continued)

(52) U.S. Cl.
CPC .............. *A61B 34/20* (2016.02); *A61B 34/25* (2016.02); *G01S 5/021* (2013.01);
(Continued)

(58) Field of Classification Search
CPC . A61B 34/20; A61B 34/25; A61B 2034/2048; A61B 2034/2051; A61B 2034/2055; G01S 5/021
See application file for complete search history.

(56) References Cited

U.S. PATENT DOCUMENTS 6,577,976 B1 6/2003 Huff et al.
6,898,554 B2 5/2005 Jaw et al.
(Continued)

FOREIGN PATENT DOCUMENTS

EP 1959831 B1 7/2010
EP 1817606 B1 1/2013
(Continued)

OTHER PUBLICATIONS

International Search Report, PCT/EP2014/050462, pp. 1-4, dated Sep. 22, 2014, NL.
(Continued)

*Primary Examiner* — Ian Jen
(74) *Attorney, Agent, or Firm* — Tucker Ellis LLP (57) ABSTRACT

A data processing method for generating a compensation information for hacking or for determining the position and/or orientation of an object in space, the method comprising the following steps performed by a computer: a) acquiring a predetermined constraint information defining one or more relative or absolute positions and/or orientations of the object in space; b) acquiring position and/or orientation data of the object while the object is positioned or moved while fulfilling the predetermined constraint; and c) determining the compensation information based on the predetermined constraint information and the acquired position and/or orientation data of the object.

15 Claims, 5 Drawing Sheets

(51) Int. Cl.
    *G01S 5/02*     (2010.01)
    *A61B 34/00*     (2016.01)

(52) U.S. Cl.
    CPC ............. *A61B 2034/2048* (2016.02); *A61B 2034/2051* (2016.02); *A61B 2034/2055* (2016.02); *A61B 2034/2057* (2016.02); *A61B 2034/2059* (2016.02); *A61B 2034/2065* (2016.02)

(56) References Cited

U.S. PATENT DOCUMENTS

| | | | |
|---|---|---|---|
| 7,263,207 | B2 | 8/2007 | Lee et al. |
| 7,623,250 | B2 | 11/2009 | Moctezuma de la Barrera et al. |
| 7,744,528 | B2 | 6/2010 | Wallace et al. |
| 7,933,730 | B2 | 4/2011 | Li et al. |
| 8,108,171 | B2 | 1/2012 | Judd |
| 8,417,318 | B2 | 4/2013 | West |
| 2004/0068496 | A1 | 4/2004 | Bergman et al. |
| 2005/0020911 | A1* | 1/2005 | Viswanathan ........... A61B 6/12 600/424 |
| 2006/0169021 | A1 | 8/2006 | Silverstein |
| 2007/0151389 | A1* | 7/2007 | Prisco ................. B25J 9/1633 74/490.05 |
| 2007/0265527 | A1* | 11/2007 | Wohlgemuth ......... A61B 6/547 600/424 |
| 2007/0270685 | A1* | 11/2007 | Kang ................ A61B 17/1764 600/424 |
| 2009/0062813 | A1* | 3/2009 | Prisco ................... A61B 34/30 606/130 |
| 2010/0161129 | A1* | 6/2010 | Costa ................... B25J 9/1697 700/259 |
| 2010/0332031 | A1* | 12/2010 | Itkowitz ............... B25J 9/1689 700/245 |
| 2012/0275645 | A1* | 11/2012 | Koenig .................. A61B 5/06 382/103 |
| 2013/0231672 | A1* | 9/2013 | Paradis ................ A61F 2/4657 606/91 |

FOREIGN PATENT DOCUMENTS

| | | |
|---|---|---|
| WO | 2010071699 A1 | 6/2010 |
| WO | 2011110966 A3 | 9/2011 |
| WO | 2012001548 A1 | 1/2012 |

OTHER PUBLICATIONS

European Patent Office, International Search Report and Written Opinion for corresponding PCT/EP2014/050462, 9 pages, dated Sep. 22, 2014, NL.

Birkfellner et al, "Calibration of tracking systems in surgical environment", IEEE Transactions on Medical Imaging, IEEE Service Center, vol. 17, No. 5, pp. 737-742, Oct. 1, 1998, Piscataway, NJ, US.

Lacey et al, "Mixed-Reality simulation of minimally invasive surgeries" IEEE Multimedia, IEEE Service Center, vol. 14, No. 4 pp. 76-87, Oct. 1, 2007, New York, NY, US.

Ming et al, "Spatial Motion Constraints using virtual fixtures generated by anatomy", IEEE Transactions on Robotics, IEEE Service Center, vol. 23, No. 1, Feb. 1, 2007, Piscataway, NJ, US.

\* cited by examiner

ESTIMATION AND COMPENSATION OF TRACKING INACCURACIES

RELATED APPLICATION DATA

This application is a national phase application of International Application No. PCT/EP2014/050462 filed Jan. 13, 2014, published in the English language.

FIELD OF THE INVENTION

The present invention is directed to the estimation and optionally also to the compensation of tracking inaccuracies, for example by generating compensation information which can be used when tracking a device to determine a more accurate position of the device. More particularly, an embodiment concerns the correction of a determined or tracked position and/or orientation of a specific point or device, determined using a tracking system, by using a position-dependent and/or orientation-dependent bias or bias-field.

BACKGROUND OF THE INVENTION

Tracking systems are well established within navigation technologies and have to be calibrated before they can produce reliable tracking information. These calibration procedures are usually performed within an idealized set-up to minimize calibration errors. During the intra-operative use of a tracking system, several error sources may occur, e.g. de-calibrations of the tracking volume because of changing physical conditions like heat effects, mechanical distortions of the camera or tracking system, inhomogeneity of physical parameters, such as distortions of electromagnetic fields or different light conditions in the tracking volume, systematic and statistical errors in marker detections, etc. Those de-calibrations may affect the accuracy of the tracking system.

In general, calibration works in a generic way and aims to minimize inaccuracies in the tracking procedure. However, in many cases systematic errors remain in the particular use of the tracking system. A generic calibration procedure is not able to solve the problems resulting from changing circumstances.

On the other hand, individual calibration procedures are quite time consuming and in many cases can only be performed by trained specialists. Thus, it is often not possible to fine-tune the calibration for particular operation cases.

PRIOR ART

It is known to use multiple sensors in the context of hybrid tracking systems and combining the tracking information to optimize the visibility and accuracy of the overall tracking procedure. Hybrid tracking systems are described in U.S. Pat. No. 6,577,976 B1, EP 1 959 831 B1, US 2006/169021 A1, WO 2010/071699 A1, US 2004/068496 A1, and U.S. Pat. No. 8,108,171 B2. Information from different sensors is used to optimize the tracking.

An estimation of bias fields is in particular important when using electromagnetic systems, since the accuracy of these systems is often degraded due to inhomogeneity of the electromagnetic field which, however, is crucial for measuring the position of the markers. EP 1 817 606 B1, EP 1 959 831 B1, WO 2011/110966 A3, and WO 2012/001548 A1 describe methods to estimate and compensate error sources within such electromagnetic systems.

U.S. Pat. No. 7,744,528 B2, U.S. Pat. No. 7,623,250 B2, and U.S. Pat. No. 7,933,730 B2 describe the use of image information to compensate for localization errors. All of these methods try to optimize the localization procedure by using multiple images from different orientations but do not directly estimate or compensate a systematic bias in the tracking system.

U.S. Pat. No. 7,263,207 B2 teaches to estimate intrinsic calibration parameters for the video camera itself by using principal markers.

U.S. Pat. No. 8,417,318 B2 discloses a method for removing position-dependent bias from tracking systems which computes invertible transformations between a tracking system and a reference system, and applies an inverse of the transformation to measurements in the tracking system to estimate the locations of reference points in the reference system and to determine relative bias at the measured points.

U.S. Pat. No. 6,898,554 B2 discloses a method for detecting a fault in a physical system which uses a model of the physical system and calculates estimated depending variables or conditions for the system using substantially only independent variables that are measured from the system using hardware redundancy.

OBJECT OF THE INVENTION

It is an object of the present invention to improve the accuracy of a tracking system.

This object is achieved by the subject-matter of the independent claims. The dependent claims are directed to advantageous embodiments. Different advantageous features can be combined in accordance with the invention wherever technically sensible and feasible. A feature of one embodiment which is functionally identical or similar to a feature of another embodiment can in particular replace the latter feature. The feature of an embodiment which supplements a function of another embodiment can in particular be added to the other embodiment.

Definitions

Hereinafter an explanation of terms used to describe the invention is given.

Marker

It is the function of a marker to be detected by a marker detection device (for example, a camera, electromagnetic sensors, an ultrasound receiver or analytical devices such as CT or MRI) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or circular shape and can therefore be referred to as a marker sphere; markers can however also exhibit a cornered, for example cuboid, shape.

Reference Star

A "reference star" refers to a device with a number of markers, advantageously three or more markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star in particular features a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

Marker Holder

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

Marker Device

A marker device can for example be a reference star or a pointer or a single marker or a plurality of (individual) markers which are then preferably positioned or attached in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

Pointer

A pointer is a rod-like instrument which comprises one or more—advantageously three or more—markers fastened to it and which can be used to measure off individual co-ordinates, in particular spatial co-ordinates (i.e. three-dimensional co-ordinates) including translational and/or rotational degrees of freedom, on a part of an object or body, wherein a user guides the pointer (in particular, a part of the pointer, e.g. the tip, which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (in particular, the tip of the pointer) is in particular known. The surgical navigation system then enables the location and orientation (of the three-dimensional co-ordinates) to be assigned to a predetermined body structure, wherein the assignment can be made automatically or by user intervention.

Navigation System

The present invention is also directed to a navigation system for computer-assisted surgery. This navigation system preferably comprises a computer for processing the data provided in accordance with the data processing method as described herein. The navigation system preferably comprises a detection device for detecting the position of the detection points in order to generate detection signals and to supply the generated detection signals to the computer, such that the computer can determine the absolute main point data and absolute auxiliary point data on the basis of the detection signals received. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). An example of a display device is an augmented reality device (also called augmented reality glasses) which may be used as goggles for navigating. A specific example of such augmented reality glasses is Google Glass (trademark of Google Inc.). An augmented reality device may be used to both input information into the computer of the navigation system by user interaction and to display information outputted by that computer.

Motion Constraint(s)

A motion constraint can be any kind of constraint or limitation which reduces the possibility that an instrument or a specific part or point thereof can be moved totally free, for example in every direction and/or can be orientated in any possible way. This constraint can either be based on a predefined fixed or mechanical relationship and/or on a specific behavior or motion sequence performed with the instrument. The motion constraints can be absolute motion constraints, such as for example pivoting a pointer while the tip of the pointer is positioned at a fixed and known location, or can be relative constraints. Regarding relative constraints, some information can remain unknown, for example it is known that the tip of an instrument remains fixed, however, the actual position of this fixed point is unknown.

In case of additionally provided information, such as for example a sensor information or the knowledge of a given position of a fixed reference point impairing the free motion of an instrument, this additional information provides a constraint that preferably only needs to be accurate within a certain degree.

Free Parameters of Estimation Procedure(s)

Parameters which are only required for the estimation procedure (estimating or calculating a bias field), but which are neither directly given in the motion constraints nor being part of the bias field, are considered to be (free) parameters of the estimation procedure. A free parameter of an estimation procedure can for example be an a-priori unknown position of a fixed point or can be a fine estimate of a motion constraint which may differ to a measured or initially specified information.

Such free parameters of the estimation procedure do not refer to parameters which are contained in the bias field itself.

Parameters of a Bias Field

Parameters of a bias field are parameters which define the bias fields, for example by specifying for each three-dimensional point a shift defining a change in position and/or orientation. A bias field information can be a compensation information being defined as follows:

$$\text{compensation} = \begin{pmatrix} s_x(\vec{p}, o) \\ s_y(\vec{p}, o) \\ s_z(\vec{p}, o) \end{pmatrix}$$

wherein: $s_x$, $s_y$ and $s_z$ quantatively defines a shift; p defines a position (vector); and o specifies an orientation (Euler angle), e.g. of the instrument towards the tracking camera.

The compensated value can be defined as follows when considering as example the tip of a pointer:

$$\text{tip}_{compensated} = \text{tip}_{uncompensated} + s(\vec{p}, o)$$

When including deviations in orientation as well, the bias field can be defined as:

$$\text{Bias} = [R^{3\times 3}(\vec{p}, o); \vec{s}(\vec{p}, o)]$$

In this case, the compensation can be performed as follows $$\text{tip}_{compensated} = R^{3\times 3}(\vec{p}, o) \cdot \text{Tip}_{uncompensated} \vec{s}(\vec{p}, o).$$

Other types of dependencies could be included in the bias fields as well, e.g. time-dependency, dependency on single reference markers (i.e. providing bias field parameters for single markers individually), environment information measured by additional devices/sensors (e.g. lighting conditions).

Referencing

Determining the position and/or orientation is referred to as referencing if it implies informing a navigation system of said position and/or orientation in a reference system known to the navigation system.

Acquiring Data

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device, such as e.g. a data acquisition device or a camera, preferably a camera of a navigation system, to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Data Processing Method

The method in accordance with the invention is in particular a data processing method. The data processing method is preferably performed using technical means, in particular a computer. The data processing method is preferably constituted to be executed by or on a computer, in particular it is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service.

In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows to display information outputted by the computer e.g. to a user. An example of a display device is an augmented reality device (also called augmented reality glasses) which may be used as goggles for navigating. A specific example of such augmented reality glasses is Google Glass (trademark of Google Inc.). An augmented reality device may be used to both input information into the computer by user interaction and to display information outputted by that computer.

Computer Program

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). A computer herein is a technical computer which comprises in particular technical, in particular tangible components, in particular mechanical and/or electronic components. Any device mentioned herein is a technical, in particular tangible device.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

The invention also relates to a navigation system for computer-assisted surgery, comprising:

the computer as mentioned above;

a detection device, such as e.g. a camera or electromagnetic sensors, for detecting the position and/or orientation of an object and to supply the position and/or orientation data to the computer; and a user interface for receiving data from the computer in order to provide information to the user, wherein the received data are generated by the computer on the basis of the results of the processing performed by the computer.

SUMMARY OF THE INVENTION

The present invention is directed to a data processing method for generating a correction or compensation information for determining the position and/or orientation of an object, preferably when using a navigation system. The compensation or correction information can be any kind of information specifying for example for each point or volume area in space and/or for each orientation of a tracked object a information for correcting a position and/or orientation determined for an object or a device. The correction or compensation information can for example be in the form of a mathematical formula depending for example on the determined uncorrected position of the object and delivering or specifying a compensation information, such as for example a translation or shift in space, to be applied on the measured position of the object to obtain a corrected position, which corrected position should better match or preferably exactly define the actual position of the object or device. The compensation information can for example define a bias being for example a systematical error or translation between a measured and an actual position, which bias can vary depending on the measured uncorrected position and/or orientation, thus defining for example a bias field.

According to the invention, additional information is used to estimate or determine the compensation or correction information or the bias field. This additional information can be obtained from a single measurement or a series of measurements made to determine the position and/or orientation of an object or a specific point of an object, the measurements being for example made when the object is moved having at least one motion constraint. Such a motion constraint can for example be the pivoting of an instrument or point a device around a defined or single point. For example, the tip or any other specified point of an object, instrument or pointer can be fixed to this point or can be brought at the point in direct contact with this point while moving the instrument. The specific point with which the instrument is brought into contact with does not need to be connected to the instrument. The pivot point can be arbitrary in space and is preferably fixed during a calibration procedure in relation to a navigation system or camera coordinate system or another reference coordinate system, which can for example be defined by a fixed or moveable and trackable calibration device. The camera, navigation system and/or reference coordinate system is preferably known a priori to provide sufficient accuracy.

The basic procedure to move or pivot an object or instrument can involve a free movement or movement according to a predefined movement sequence, for example with respect to a fixed or moving calibration point having a fixed or permanent determinable position in space. This movement procedure can be similar to a standard instrument calibration procedure. Preferably not only a fixed calibration information is stored for the particular instrument, but the parameters of a locally varying bias field are calculated based on the observations or determinations of the position and/or orientation of the moved instrument considering the additional constraints, such as e.g. movement constraints.

If for example such a pivoting operation is performed and the tip or a specific point of an object has some known motion constraint while performing this operation or movement, and the camera or navigation system determines, based on measured values, that the object or instrument has such a position and orientation in space that the tip is moving, contrary to the actual situation, then a correction information or bias field can be calculated, at least for every measured position and/or orientation, in order to correct a measured position and/or orientation, so that the pre-known motion constraint is met.

Using for example an interpolation and/or extrapolation operation, the correction or bias information or bias field cannot only be determined for the measured positions in space, but can also be extended to a larger area, as e.g. an expected area of surgical treatment or even the whole space.

This bias field being e.g. a map of position-dependent and/or orientation-dependent biases or translations can be stored and can be used for subsequently correcting tracking errors.

The bias field can for example include local variations as well as orientation dependencies. For example, an estimation of a localization error can depend on the directional angle between the camera or another reference coordinate system and the instrument.

Additionally, the bias field can be calculated for various types of objects including the camera itself, for example by performing measurements as described above to determine and quantify the overall inhomogeneity in the camera volume. Further, the bias field can be calculated for specific navigated instruments, so that for example for each instrument having performed a calibration or correction determination process as described above, a separate instrument-specific correction information or bias field is determined.

It is possible that a correction information or bias field can be determined for a single marker, preferably when considering this single marker in combination with other markers having a fixed relationship to this single marker, for example when considering a reference star. Some error or correction terms can for example be related to the inhomogeneity in the reflectivity of one or more particular markers. Thus, it can be advantageous that a correction information or bias field is determined or analyzed and stored in relation to the respective particular marker(s).

In order to separate standard observational information from the bias field, it is advantageous to describe the bias field with a limited set of parameters (e.g. using polynomial approximations, splines, etc.), since the observations (motions of tracked objects) usually are not restricted to a certain amount of parameters. This provides the advantage to robustly estimate the parameters of the bias field model. The bias field is preferably modeled as a slowly varying field (regarding local variation and orientation dependence) which can be represented by a limited set of parameters. Alternatively, it can be described using additional regularization terms which penalize high variations in the field. In both cases, the model assumes that certain types of errors (in particular, high local variations) are unlikely and cannot be detected robustly. An upper limit for variations can be provided, specifying e.g. a maximum change of the correction term or value per a given distance. In case an approximation algorithm and/or the performed measurements deliver a correction term above this upper limit, this correction term can e.g. be "smoothed" or interpolated using neighbouring correction terms.

Further on, the more constraints are used, the better are the options to estimate the parameters of the bias field. Of course, this may depend on an appropriate selection of constraints, which help to robustly identify the parameters of the bias field as well as the amount of observation (tracking) data which are available to identify the parameters for a specific bias estimation task. As already mentioned, motion constraints are one embodiment to allow the bias estimation. Within a specific workflow step, the navigation system can request that the user fixes the tip of an instrument at a reference point and moves the instrument in a specific way (e.g. by pivoting around the point or by rotating the instrument which can be axially fixed in another tracked instrument). The reference point can be simply a fixed point in the camera coordinate system, e.g. a point on the patient, a point on a reference array rigidly fixed to a tracked structure (e.g. bone), or the operating table, while the camera and/or the table/patient is kept fixed during the movement. Alternatively, the point can be defined in relation to another tracked instrument which is known to have an appropriate reference array with sufficient accuracy. In particular, a specific point in a bore or notch in a calibration device with known relation to the reference array of this device can be used. The movement of the instrument/pointer device around this point should be performed in a way that a robust estimation of a particular bias field can be achieved (e.g. sufficient range of rotation around the pivot point). This can be communicated to the user and/or automatically detected/controlled during or after the pivoting procedure.

The pivot point or other geometric reference information may be known a-priori, e.g. when the position of a pivot point is known in relation to the reference array of a tracked calibration device or as a specific landmark on the anatomy or another structure in relation to a reference array fixed to the anatomic structure (e.g. a landmark on the bone or a reference point on the array itself). In this case, the specific geometric information can be used in the bias field model. Otherwise, the constraint has to be limited to the information that a certain point (or other geometric object like an axis) is fixed during the motion without knowing its precise location.

Different types of bias fields can be estimated depending on the robustness of the achievable parameters. For example, the bias field can focus on directional dependences, i.e. the bias field only models errors/correction factors according to the directional alignment between the camera (or another reference coordinate system) and the instrument/pointer device with no or only limited spatial variation of the bias field. Otherwise, the bias field could also include spatial variations in various directions. This could e.g. be achieved for single markers within a reference array of an instrument or pointer device. In this case, further restrictions given by the entire reference geometry (known geometric relationships) may allow to robustly estimate spatial variation of the errors in the detection of a single marker. As already mentioned, the bias field can be modeled, stored and used to compensate different types of objects and errors including the overall camera calibration error (inhomogeneity in the camera volume), accuracy of single markers as well as directional and/or spatial varying of specific instruments in relation to the camera system and/or other reference geometries/coordinate systems like the coordinate system of a calibration device or a reference array attached to an anatomical structure or the coordinate system of the instrument itself.

The estimation procedure can be performed/repeated at different steps during the use of the tracking/navigation system and thus allows individual calibration of instruments, OR setups, etc. which do not need to be performed by specifically trained persons. It can be easily integrated into the overall workflow of the particular use case and performed at a time close to the use of the specific instrument to minimize inaccuracies which may result because of timely changing parameters of the bias field (e.g. because of changes in the camera temperature or lighting conditions which may affect the overall accuracy).

In addition to the motion constraints, also other constraints can be used to make the estimation of the bias field more robust and/or to increase the option to include more parameters in the model of the bias field. This could be the use of additional sensors (e.g. gyroscopic or inertial sensors) which can add further constraints on the consistency between the motion detected by the optical tracking system and the additional sensors, e.g. the acceleration values have to be consistent between the optical tracking (acceleration calculated from the tracking data) and the inertial sensors (directly measured acceleration). Additionally, noise parameters/filtering procedures like Kalman filters can be included in the estimation model, which ensure that a smooth motion path and/or a minimization of noise across the entire time series of tracking data is established. The distances and angles within a marker geometry and/or other known relative or absolute geometrical information can be used to constrain the estimation model, i.e. the tracked information is preferably consistent with the known geometrical information and this information can be used as a constraint in the bias field estimation model/process. This could also include tools, which are specifically designed for the estimation of bias fields being e.g. similar to the Accuracy Assessment Kit (AAK) provided by the camera manufacturer NDI to check the homogeneity of the camera field. These specific tools could e.g. be equipped with a tip or other attachment which can be used for pivoting or other constraint motions.

Beside other (tracking) sensor types, also other image information can be used in the estimation process to provide further constraints. For example, image information from tracked 2D video cameras, 2D x-ray images, or 3D scan data (e.g. CT or MRI data) can be used. These image data is preferably acquired using tracking/registered image acquisition procedures (e.g. registered intra-operative x-ray images acquired with a tracked fluoroscopic/C-arm device or intra-operative CT/MRI scanner). The constraints may be obtained by using known relationships between the image data and geometric information known in relation to the tracking system or by obtaining images from different directions and establishing the consistency between the series of image data. Methods for providing and algorithms for detection of appropriate reference structures can be included. For example, an automatic detection of anatomic reference points or references objects like implanted screws can be included for intra-operative image data and/or optical projection lines projected onto a particular surface by a projector device can be used for obtaining correspondences in video data.

Another type of motion constraint which can be used for the estimation of the bias field can be obtained by using the following procedures. A movement of the camera for a fixed set-up (i.e. fixed relationships between certain reference arrays) is performed and differences in the tracked coordinates are analysed. For this purpose, again redundancies in the tracked information can be used to obtain additional constraints which can be used for the bias field estimation. This can be any constraint mentioned in the description of this invention (e.g. known geometric relationships according to the marker geometries in the reference arrays, additional sensors, etc). Additionally, further constraints can be achieved by ensuring a fixed (but possibly unknown) relationship between different reference arrays, i.e. the position of the reference arrays is kept fixed in a specific setup and the camera is then moved around. In this context, one reference array can be used as a basic/accurate reference ("gold standard reference") and the bias field can be obtained for the other array. This approach can e.g. be used when a large reference array, which is known to be more accurate, or when a reference array, which is known to be more stable (regarding the tracking) because it uses specific markers like flat markers which are known to be less dependent on the orientation between camera and reference array, is available and can be used as a basic reference. In particular, this is often the case when using intraoperative imaging systems like intraoperative CT scanners with flat markers attached to the scanner. In this case, the flat markers are usually widely spread around the scanner and thus provide a larger and more accurate reference. Alternatively, the bias estimation field can be obtained for the overall constellation (without having any basic/gold standard reference) and only the information about the static setup is used as a motion constraint.

Also specifically known motion paths or restrictions in the motion area could be used to obtain motion constraints. For example, during imaging procedures it is known that scanner gantry only moves in a certain direction (only in the direction of the scanning table) during the scan. The information that the movement of the reference array only goes in one specific unknown direction can be used to estimate the bias field according to this motion. Additionally, information about the orientation of the data set and in particular, the relation between the flat markers attached to the scanner gantry and the marker array (e.g. marker array is orthogonal to the orientation of the image data set) can be used. For C-arms (in particular 3D C-arms), the information can be used, that the C-arm rotates around a specific axis or within a specific plane which is known or unknown. In all these cases, the information from a previous calibration of the imaging device (in relation to the reference array) and/or the information in the image data set can be used as additional information for the estimation of the bias field.

Besides a full compensation of the bias field, the information can also be used to dynamically assess (during the navigation procedure or during the calibration/bias field estimation process) whether crucial errors e.g. for single markers, reference arrays e.g. exist. This information can then be used to detect specific error sources and/or to provide information to the user about existing inaccuracies and/or measures which have to be taken to ensure accurate navigation. These measures can e.g. be a replacement of single markers, re-calibration of the camera, replacement of instruments, etc.

BRIEF DESCRIPTION OF THE DRAWINGS

The invention will be described in more detail by reference to exemplary embodiments, wherein.

DETAILED DESCRIPTION OF THE EMBODIMENTS

Figure 1:
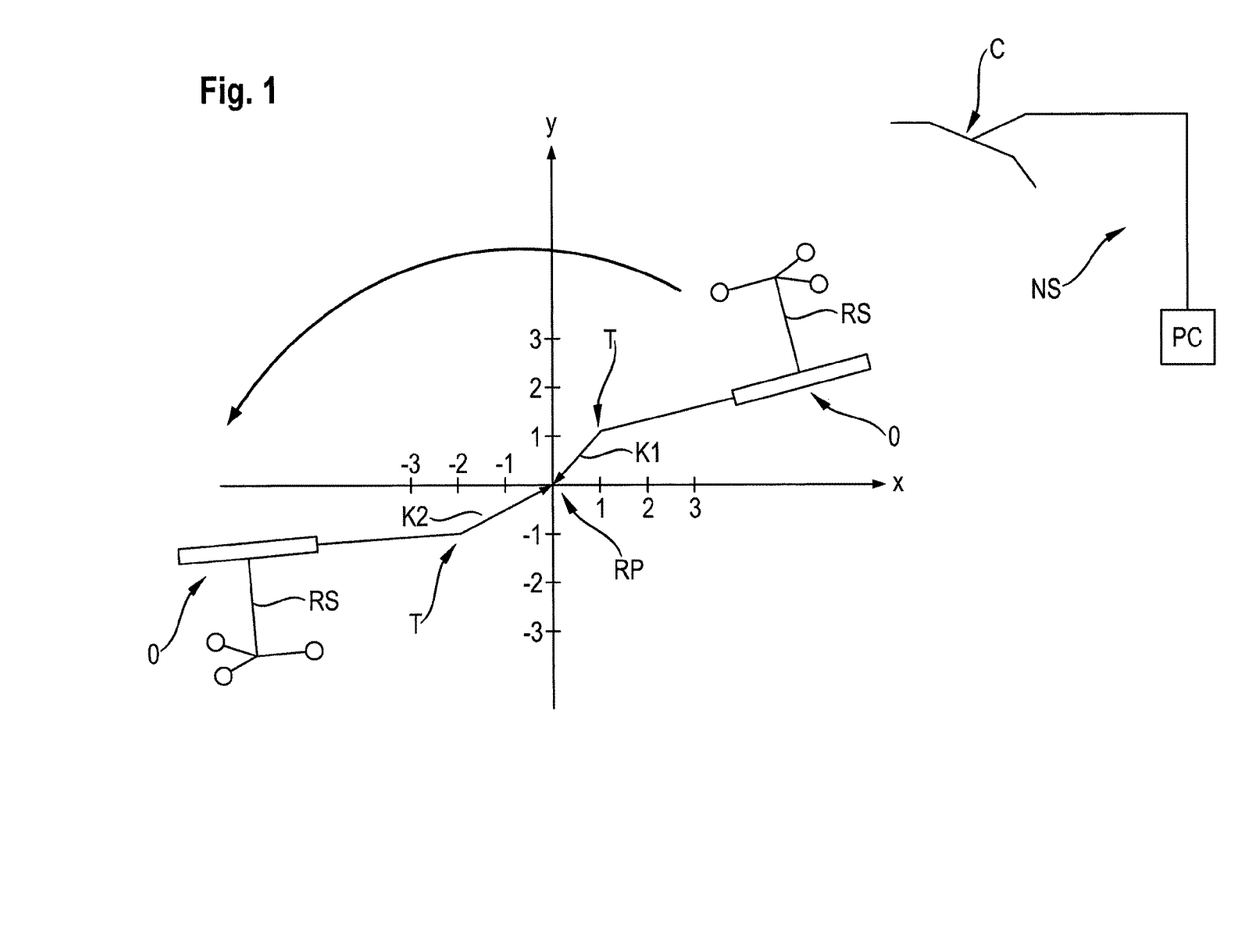
FIG. 1 shows the principle of the present invention in two-dimensional space.

The workflow for generating compensation information is illustrated in FIG. 1 using a simple two-dimensional example for explanatory purposes only. It is appreciated that the invention can be performed also in three-dimensional space using the illustrated described principles.

An object O being a pointer having a pointer tip T is moved fulfilling a pre-defined motion constraint, the motion constraint being that the pointer tip T is always located on a reference point RP having a fixed position in space. Besides that, the object or pointer can be moved freely, i.e. the pointer is pivoted around the fixed reference point RP.

A reference star RS is fixedly connected to the pointer and the position of the pointer tip T in a first position is determined by determining the position of the reference star RS using a well-known navigation system NS having cameras C to detect the markers of the reference star RS and calculating from this position and a referencing information, said referencing information informing the navigation system NS of the shape or geometric dimensions of the object, the position of the tip T shown as the first uncorrected position P1 having (x, y)-coordinates (1,1).

Since it is known, due to the motion constraint, that the pointer tip T cannot be at the position P1 (1, 1), but must be at the position of the reference point, which can be a reference point having an unknown position or having (to simplify the explanation) the known position RP (0, 0), a correction information K1 (−1, −1) can be calculated defining that if the tip T is determined to be at the position P1 (1, 1), then the correction information K1 (−1, −1) defining a shift in space has to be applied, to obtain a corrected value (0, 0) for the position of the tip T in space. The correction information K1 (−1, −1) is stored as bias value for the measured position P1 (1, 1).

If the pointer or object O is moved to a second position, as indicated by the arrow, to now be on the left side of FIG. 1, the same process is performed. The navigation system determines the position of the reference star RS and using the additional reference information of the object O, a position of the pointer tip T in space is determined to be at location P2 (−2, −1). Since, same as above, due to the motion constraint it is known that the tip T of the pointer O must be at the position of the reference point RP (0, 0), a second correction information K2 (2, 1) defining another shift in space can be calculated, so that when the navigation system NS determines the position of the tip T to be at location P2 (−2, −1), then this second correction information K2 (2, 1) being for example a vector having a specific direction and length can be applied to the measured value (−2, −1) to obtain a corrected position value (0, 0). The correction information K2 (2, 1) is stored as bias value for the measured position P2 (−2, −1).

For a later on measured position of for example P3 (−0.5; 0), the correction value K3 can be calculated by interpolating between K1 and K2, thus obtaining (+0.5; 0).

In other words, if a number of movements or measurements of an object O is made while knowing that the object is moved having a specific motion constraint, then correction values K1, K2, ..., KN further probably also specifying a change in orientation for a number of positions in three-dimensional space can be found. Using well-known interpolation and extrapolation algorithms, a bias field covering the whole three-dimensional space can be determined.

Figure 2:
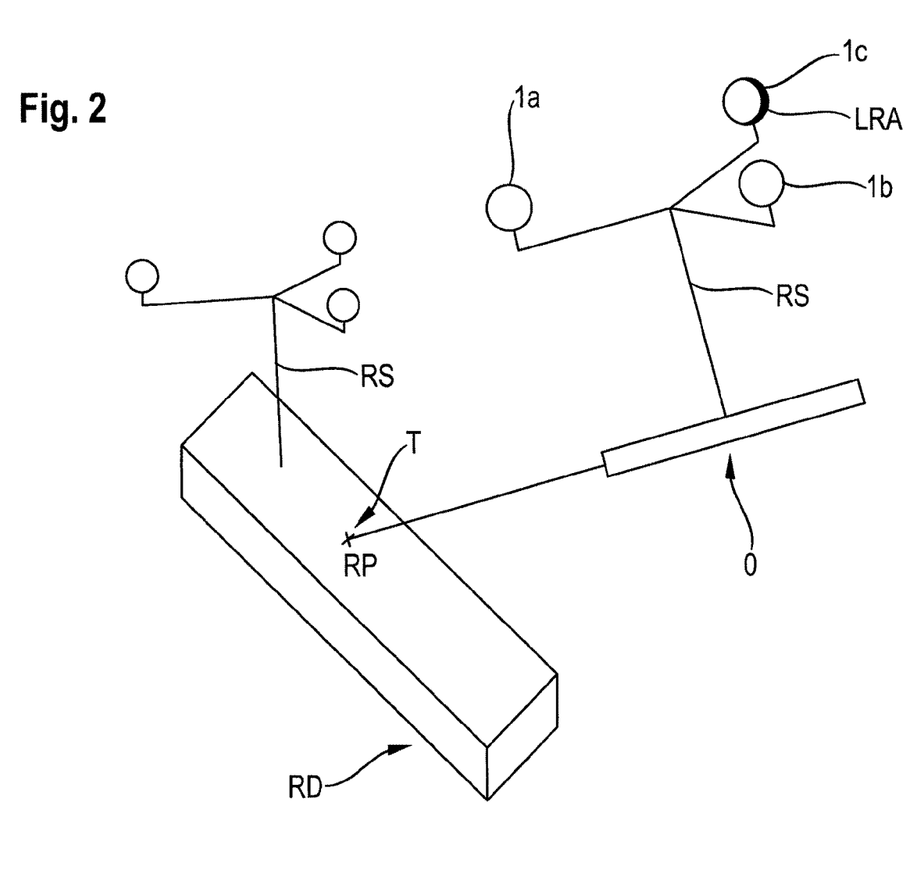
FIG. 2 illustrates a process for determining a bias field.

FIG. 2 shows an exemplary embodiment of the present invention, wherein an object O being a pointer is connected to a reference star RS to which three individual markers 1*a*, 1*b* and 1*c* are connected via marker holders. The pointer has a tip T which is brought into contact with a referencing device RD being itself connected to a reference star RS. A navigation system can now be informed that the pointer 0 is moved with respect to the referencing device RD having the motion constraint that the pointer tip T always points at a reference point RP being for example a notch on the reference device RD, i.e. the pointer 0 is pivoted around the reference point RP.

In this embodiment it is not required that the reference point RP has a fixed position in space, since the position can always be determined by the navigation system based on the registration or calibration information of the referencing device RD in combination with determining the position of the reference star RS being connected to the referencing device RD. Instead, the position needs to be fixed or otherwise uniquely defined by a motion constraint according to the coordinate system of the reference device.

All markers of the referencing device and the pointer can basically have a shape of reflecting spheres. In case one marker (in the example marker 1*c*) has a less reflective area LRA, the position of the marker 1*c* will correctly be determined in the center of the viewed reflective surface, when the marker 1*c* is viewed by the camera of the navigation system from the fully reflective area (i.e. in FIG. 2 from the left side). If, however, the camera of the navigation system gets to view the marker 1*c* from an angle so that the less reflective area LRA comes into the line of sight of the camera, the position of the marker 1c will be determined incorrectly, since the calculated center of the reflecting surface does not correspond to the center of the marker 1c anymore. This effect can also be considered and corrected using the process illustrated and described with reference FIG. 1 for obtaining correction information and calculating a bias field.

In general, the estimation of a bias field being composed of a number of bias or correction information or values, may be performed by determining the parameters of the bias field directly, i.e. the estimation of the bias field does not need additional parameters which are not included in the bias field itself.

Alternatively, the estimation of the bias field may be performed by including additional parameters which are necessary for estimating or identifying (parts of) the given but unknown constraint information, e.g. when the position of a fixed point is not predetermined (its location is not known) but needs to be determined during the estimation process. Similar parameters can also be necessary for other scenarios, e.g. when the consistency between sensor information and tracking data needs to be determined or rated. These additional parameters can be considered to be (free) parameters of the estimation procedure which need to be estimated during the determination of the bias field, but which are not included in the bias field itself (i.e. those parameters are not part of the information which is necessary for compensating the tracking data).

The knowledge about the reference point can be different for the application of different bias estimation methods. It has to be considered whether the motion constraint provides an absolute or relative information.

When talking about absolute constraints, it is assumed that all relevant information, which should be known for the motion constraint, is completely fixed (i.e. there are no parameters, e.g. the position of the fix or fixed point(s) of the motion, which are not known a-priori but need to be determined during the entire estimation process) and accurate. This is for example considered to be the case when all relevant reference points are known according to locations defined by a calibration/referencing device, i.e. the calibration device acts as a reference for these positions. For absolute constraints, the estimation of the bias field focuses on the determination of the parameters of the bias field and takes the absolute constraints (e.g. position of the reference point) as fixed data, which are not modified during the bias field estimation.

When talking about relative motion constraints, some free parameters remain in the estimation procedure which are necessary to identify (parts of) the motion constraint in the data. In this case the motion constraint is fixed, but not all information about the motion constraint is known to the system or procedure in advance. Thus, these parameters are designated as being unknown motion parameters and represent free parameters of the estimation procedure. This is for example the case when the position of the reference/fixed pivot point is unknown. This can also be the case when the constraint only describes a relative motion between objects where none of the objects provides a clearly defined coordinate system. In this case, a combined strategy for estimating the unknown motion parameters and the bias field needs to be applied. The union of unknown motion parameters and bias field parameters are subsequently called free parameters. In this case, the estimation can be either of the following:

i) Sequentially, i.e. the unknown motion parameters/free parameters of the estimation procedure (e.g. the 3D position of the reference point) are determined in the first step and then the parameters of the bias field are estimated (this could also include iterations of these steps).

ii) In a coupled way, where one optimization procedure is applied, which determines the free parameters of the estimation procedure and the bias field parameters in parallel. In this case, both types of parameters are optimized in the estimation procedure. Option i) could also be used to determine an appropriate initialization of the unknown parameters before starting the optimization procedure.

iii) In a combined way, where e.g. option i) is used for finding initial or approximate solution and option ii) is used for refining this approach.

The above optimization steps and strategies can also be used when motion parameters are basically known but cannot be accurate enough, e.g. when only a rough estimation of the 3D position of the motion fixed point is available, but this position should be refined during the optimization procedure. In this case, the initial knowledge can be used as an initialization of the optimization procedure (similar to option iii) above). Additionally, the (approximate) knowledge about the unknown or not precisely known motion parameters can be included in the overall optimization measure in a way, that situations where these parameters drift off too much from the approximately known parameters are prohibited or penalized.

Figure 3A:
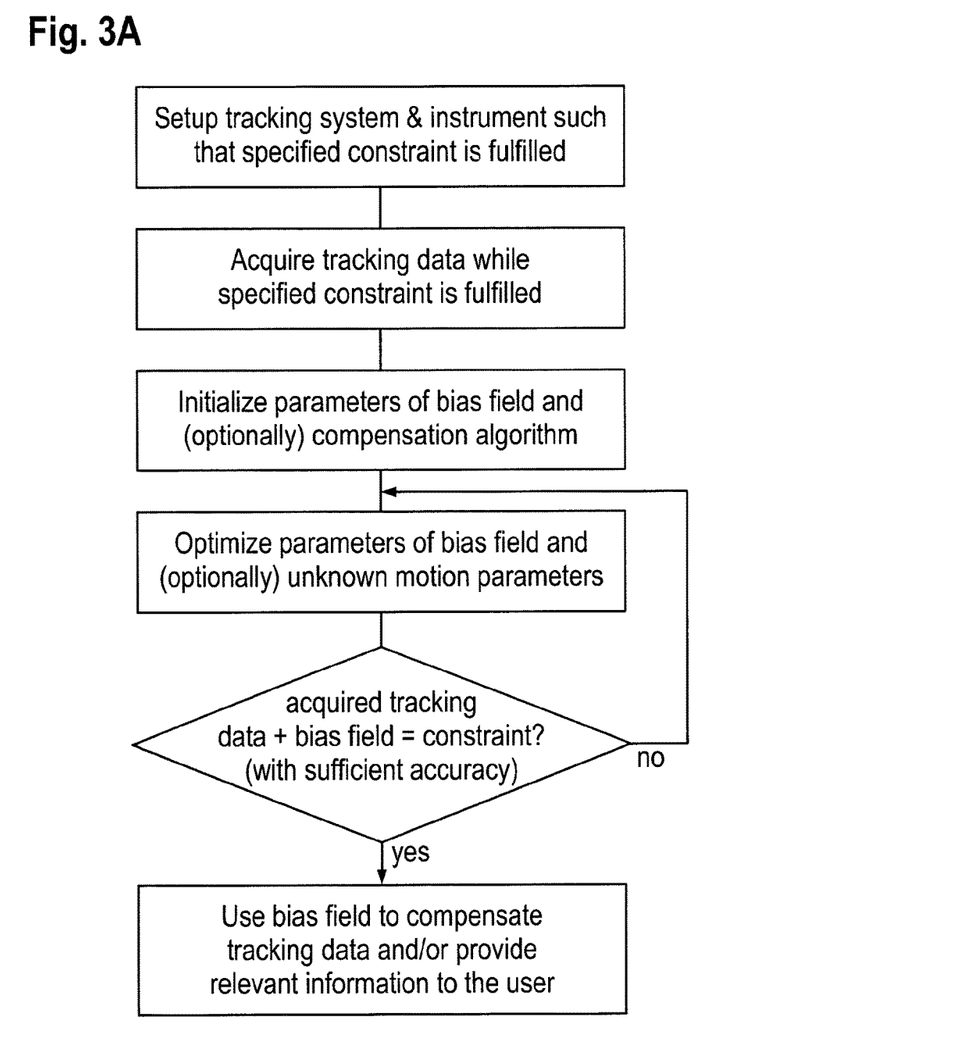
FIG. 3A is a flowchart of an exemplary embodiment of the invention.

FIG. 3A illustrates a data processing method according to a general exemplary embodiment of the invention. In a first step, the tracking system and instrument is set up such that a specified constraint is fulfilled. In the next step, tracking data is acquired while this specified constraint is fulfilled, for example the instrument is moved and/or its orientation is changed while fulfilling this specific constraint. The parameters of a bias field and optionally of a compensation algorithm are initialized. Using the acquired tracking data and the knowledge about the specified constraint, the parameters of the bias field and optionally of the mentioned unknown motion parameters/free parameters of the estimation procedure are optimized. In the subsequent step, it is determined whether or not the acquired tracking data meets the constraint with a predefined sufficient accuracy when applying the so far optimized (parameters of the) bias field.

If the constraint is not fulfilled with sufficient accuracy, the method is iteratively performed by optimizing the parameters of the bias field and optionally the unknown motion parameters/free parameters of the estimation procedure again to obtain a new bias field and to determine again whether or not the constraint is met with the required accuracy. This process is performed iteratively until the constraint is met with sufficient accuracy, so that the bias field can subsequently be used to compensate tracking data or to provide relative information to the user.

Figure 3B:
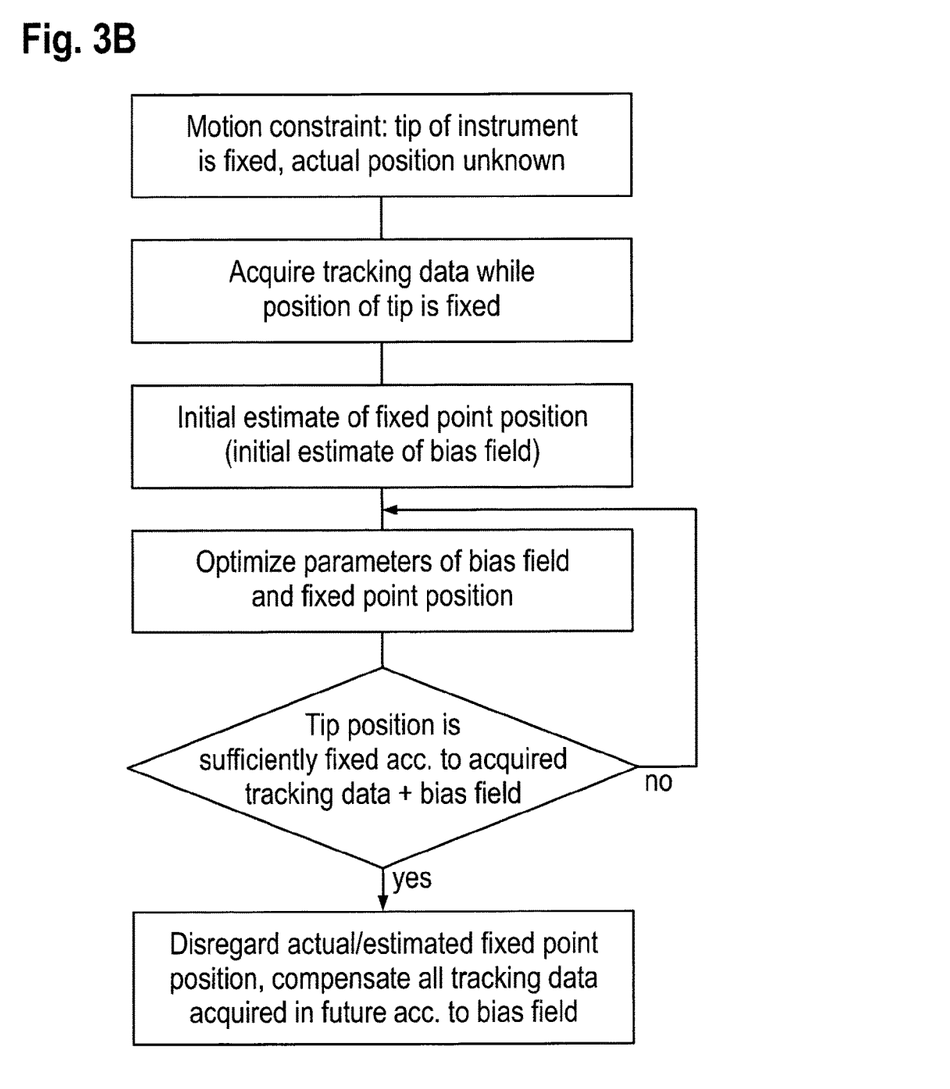
FIG. 3B is flowchart for a specific example of the general flowchart of FIG. 3A.

FIG. 3B is a more specific example of the general method illustrated in FIG. 3A, so that reference is made to the above description.

As an example, the motion constraint is that the tip of an instrument (for example a pointer) is fixed, however, the actual position of the fixed tip is unknown. It is noted that the tip can either be fixed by any mechanical means or can preferably be fixed by considering the knowledge that the instrument is moved in a manner while the tip is pointed to this fixed position. The tracking data is acquired, as mentioned above, while the position of the tip is fixed. Subsequently, the fixed point position is initially estimated and optionally an initial estimate of the bias field can be made.

Then, the parameters of the bias field and the fixed point position is optimized (an example is described below with reference to FIG. 4). It is then determined whether or not the tip position is sufficiently fixed according to the acquired tracking data when additionally considering or applying the bias field (parameters). In other words, the acquired tracking data is used to calculate the tip position and the bias field is used to correct the thus calculated tip position. If the tip position is sufficiently fixed (for example for a number of different positions and/or orientations of the instrument), then the thus determined bias field can be used to compensate all future acquired tracking data, wherein the actual or estimated fixed point position can be disregarded (i.e. the information about this fixed point position is not needed any longer once the bias field is determined).

However, in case the tip position is not sufficiently fixed in a previous step, even when considering the bias field, then another optimization has to be performed for the parameters of the bias field and optionally of the fixed point position. This again has to be performed iteratively until the tip position is sufficiently fixed.

Figure 4:
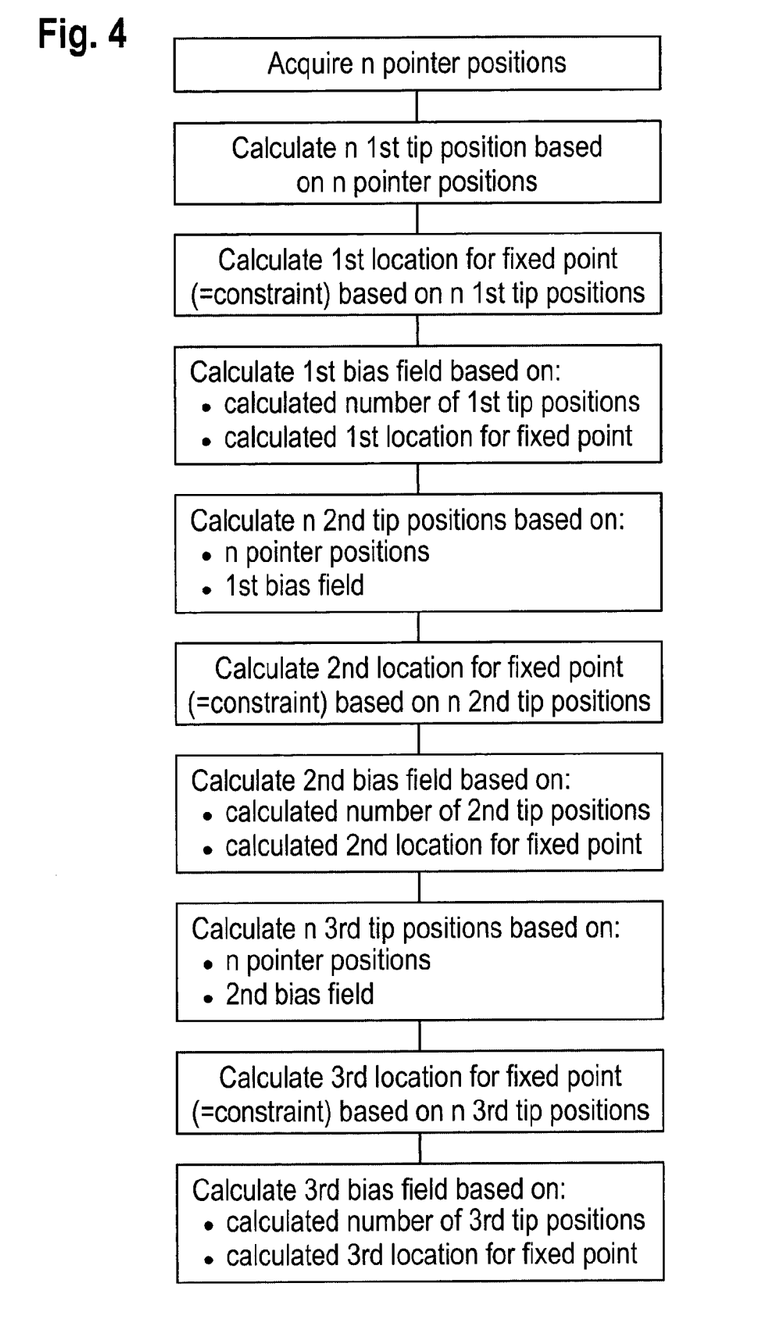
FIG. 4 is a flowchart for an example to iteratively calculate a bias field.

FIG. 4 illustrates a method for optimizing the parameters of a bias field and estimating or optimizing the position of a not previously known fixed point. It is assumed for the whole process that a predefined motion constraint is met such as for example the tip of a pointer is moved around a fixed point which has an actual unknown position.

In a first step, n pointer positions and orientations are acquired. Based on an initial set-up or initial estimate, n first tip positions and orientations are calculated based on the acquired n pointer positions and orientations. Based on the n calculated first tip positions and orientations, the first location for a fixed point (constraint) can be calculated using for example a least squares method. Based again on the calculated number of the n first tip positions and orientations and in addition using the calculated first location for the fixed point, a first bias field (first bias field parameters) is calculated.

Using this thus calculated first bias field and the n acquired pointer positions and orientations, n second tip positions and orientations can be calculated. Based on these calculated n second tip positions and orientations, a second location for the fixed point (constraint) is calculated, which may differ from the first location for a fixed point. Using this calculated second location for the fixed point and the calculated number of n second tip positions and orientations, a second bias field can be calculated.

This process can be repeated until a predefined criterion is met, wherein FIG. 4 only illustrates the process up to the calculation of a third bias field. It will be appreciated that using the illustrated concept a fourth and so on bias field can be calculated as well.

The mentioned predefined criterion for stopping this algorithm and using the last calculated bias field for subsequent procedures can for example be that the calculated n tip positions are within a specified maximum range around the calculated location for the fixed point when applying the bias field (parameters).

The described invention can be performed when having a fixed basic set-up and the instruments are moved. It is understood that the invention can also be applied when for example a camera or a camera system is moved, preferably while the setup or the instrument(s) remain fixed.

A user can be informed by the described method, for example by providing or triggering an optical and/or acoustical signal, such as e.g. displaying or providing to a display an information indicating information of the bias field or parameters thereof. For example, if a bias field (parameter) exceeds a predefined threshold, which means that e.g. more than a desired or allowed correction must be made, then such information or warning can be provided, optionally indicating measures which should be performed by a user, such as e.g. replacing one or more markers or checking the general set-up.

The invention claimed is:

1. A navigation system for computer-assisted surgery, comprising:
   a computer comprising a processor, the processor being configured to perform the steps of:
   a) acquiring, at the processor, predetermined constraint information defining one or more positions and/or orientations of an object in space;
   b) acquiring, at the processor, orientation data of the object while the object is positioned or moved while fulfilling a predetermined constraint; and
   c) determining, by the processor, compensation information based on the predetermined constraint information and the acquired orientation data of the object;
   a detection device for detecting an orientation of the object and supplying the orientation data to the computer; and
   a user interface for receiving data from the computer in order to provide information to a user, wherein the received data are generated by the computer on the basis of a result of processing performed by the computer.

2. The navigation system according to the claim 1, wherein the detection device is at least one of a camera, an electromagnetic sensor, a sensor array.

3. A navigation system setup comprising:
   the navigation system according to claim 1; and
   a sensor that is connected or fixed to the object and is configured to transmit movement or acceleration data to the computer, wherein the sensor is at least one of a gyroscopic sensor or an inertial sensor.

4. A method performed using a computer comprising a processor, for generating compensation information for tracking or for determining the position and/or orientation of an object in space, the method comprising the following steps performed by a computer:
   a) acquiring, at the processor, a predetermined constraint information defining one or more positions and/or orientations of the object in space;
   b) acquiring, at the processor, orientation data of the object while the object is positioned or moved while fulfilling the predetermined constraint; and
   c) determining, by the processor, the compensation information based on the predetermined constraint information and the acquired orientation data of the object.

5. The method of claim 4, wherein the predetermined constraint information is a motion constraint information or an information defining a pivoting operation or an information defining a motion path, each of these capable of employing free parameters in the estimation procedure.

6. The method of claim 4, wherein the predetermined constraint information is an information obtained or acquired from a sensor, the sensor can be connected to the object or the tracking system, or is the information that only a camera or camera system is moved.

7. The method of claim 4, wherein step c) of determining, by the processor, the compensation information includes the steps:

c1) determining, by the processor, an estimate value specifying the predetermined constraint information;

c2) determining, by the processor, based on the acquired position and/or orientation data of the object a possible or corresponding position and/or orientation data of the object such that the object fulfils the predetermined constraint information;

c3) comparing, by the processor, the possible or corresponding position and/or orientation data of the object with the acquired position and/or orientation data of the object and determining, by the processor, a compensation information to compensate or shift the acquired position and/or orientation data of the object, so that the predetermined constraint information is fulfilled.

8. The method of claim 4, wherein a bias field is determined by the processor based on a number of determined, by the processor, compensation information at different acquired position and/or orientation data of the object.

9. The method of claim 4, wherein the bias field is described based on an approximation of the measured bias field values.

10. The method claim 8, wherein the bias field is modelled restricted by regularization terms to restrict variations of the bias field being below a predetermined upper limit.

11. The method of claim 8, wherein the determined compensation information or bias field is stored in a database.

12. The method of claim 8, wherein the user is informed about the bias field and/or if the bias field has at least one bias or correction value being above a defined limit, a warning or text message is provided to the user.

13. A method for compensating a tracking or position or orientation data of an object in space, the method comprising the following steps performed by a computer comprising a processor:

a) acquiring, at the processor, position and/or orientation data of the object;

b) acquiring, at the processor, the compensation information generated according to any one of claims 4 to 12, the compensation information being related or corresponding to the acquired position and/or orientation data of the object; and c) determining, by the processor, from the acquired position and/or orientation data of the object and the related or corresponding compensation information a compensated position and/or orientation data of the object.

14. A non-transitory computer readable program which, when running on a computer or when loaded onto a computer, causes the computer to perform the method steps:

a) acquiring, at the processor, a predetermined constraint information defining one or more positions and/or orientations of an object in space;

b) acquiring, at the processor, orientation data of the object while the object is positioned or moved while fulfilling the predetermined constraint; and c) determining, by the processor, compensation information based on the predetermined constraint information and the acquired orientation data of the object.

15. A computer comprising a non-transitory computer readable program which, when running on a computer or when loaded onto a computer, causes the computer to perform the method steps:

a) acquiring, at the processor, a predetermined constraint information defining one or more positions and/or orientations of the object in space;

b) acquiring, at the processor, orientation data of the object while the object is positioned or moved while fulfilling the predetermined constraint; and c) determining, by the processor, the compensation information based on the predetermined constraint information and the acquired orientation data of the object.

* * * * *